United States Patent

McCallie, Jr. et al.

(10) Patent No.: US 8,239,216 B2
(45) Date of Patent: Aug. 7, 2012

(54) SEARCHING AN ELECTRONIC MEDICAL RECORD

(75) Inventors: David P. McCallie, Jr., Stilwell, KS (US); Christopher S. Finn, Liberty, MO (US); Margaret Cushing Kolm, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 733 days.

(21) Appl. No.: 12/351,288

(22) Filed: Jan. 9, 2009

(65) Prior Publication Data

US 2010/0179827 A1    Jul. 15, 2010

(51) Int. Cl.
*G06Q 50/00* (2012.01)
(52) U.S. Cl. .................................. 705/2; 705/3
(58) Field of Classification Search ............ 705/2, 3
See application file for complete search history.

(56) References Cited

U.S. PATENT DOCUMENTS

| | | | |
|---|---|---|---|
| 5,576,954 A * | 11/1996 | Driscoll | 1/1 |
| 5,893,092 A * | 4/1999 | Driscoll | 1/1 |
| 7,739,123 B1 * | 6/2010 | Rappaport | 705/2 |
| 2004/0243545 A1 * | 12/2004 | Boone et al. | 707/2 |
| 2004/0249677 A1 * | 12/2004 | Datta et al. | 705/3 |
| 2006/0179044 A1 * | 8/2006 | Rosenberg | 707/3 |
| 2007/0088695 A1 * | 4/2007 | Bleyendaal et al. | 707/5 |
| 2008/0120296 A1 * | 5/2008 | Kariathungal et al. | 707/6 |
| 2009/0178004 A1 * | 7/2009 | Stoval et al. | 715/812 |
| 2010/0131498 A1 * | 5/2010 | Linthicum et al. | 707/722 |

OTHER PUBLICATIONS

Martin Gardner. "Information retrieval for patient care". British Medical Journal (International edition). London: Mar. 29, 1997. vol. 314, Iss. 7085; p. 950.*

* cited by examiner

*Primary Examiner* — Luke Gilligan
*Assistant Examiner* — Robert Sorey
(74) *Attorney, Agent, or Firm* — Shook, Hardy & Bacon L.L.P.

(57) ABSTRACT

A method, system, and medium are provided for searching an electronic medical record. Search results are returned in response to a search query. The search query may be one or more designated medical concepts. The search results may be displayed according to a ranking that determines which search results are likely to be the most responsive to a query submitted by a particular clinician based on matching the most important clinical concepts in each document to the most important clinical concepts in the search query.

13 Claims, 9 Drawing Sheets

FIG. 7.

810—TYPE: | OFFICE VISIT
812—DATE: | OCT 4 2005
814—TITLE: MR. X, PEPPERONI PIZZA WITH HOT PEPPERS~820
816—AUTHOR: T. JONES, MD
818—SOURCE: RIVER HEIGHTS MEDICAL ASSOCIATES

REASON FOR VISIT: HEARTBURN~822

MR. X. ... WAS CELEBRATING THE OPENING OF HIS SON'S NEW PIZZERIA. HE ATE "ABOUT TWO" LARGE PEPPERONI PIZZAS WITH 824—HOT PEPPERS. APPROXIMATELY 825 AN HOUR AFTER FINISHING, HE EXPERIENCED "THE WORST HEARTBURN I EVER HAD, SO BAD I THOUGHT I WAS HAVING A HEART ATTACK~826

... HE HAS NEVER BEEN DIAGNOSED WITH GI ULCER~828

PAST MEDICAL HISTORY: HYPERLIPIDEMIA, ABDOMINAL HERNIA~830 REPAIR 2002.

FAMILY HISTORY: CARDIOVASCULAR: FATHER DIED OF HEART~832 ATTACK AT AGE 59.

MEDICATIONS: LIPITOR 40 MG DAILY. ALLEGRA AS NEEDED, SEASONALLY, FOR HAY FEVER.

|  | 822 | 825 | 826 | 828 | 830 | 832 |
|---|---|---|---|---|---|---|
| Text | Heartburn | heartburn | heart attack | heart attack | Abdominal Hernia Repair | GI Ulcer |
| Clinical Concept | SNOMED CT 16331000 (Heartburn) 913 | SNOMED CT 16331000 (Heartburn) 914 | SNOMED CT 22298006 (myocardial infarction) 915 | SNOMED CT 22298006 (myocardial infarction) 916 | SNOMED CT 84744001 (repair of hernia of abdominal wall) 917 | SNOMED CT 40845000 (gastrointestinal ulcer) 918 |
|  |  |  | *Attributes* |  |  |  |
| U Status | True | True | Ambiguous | True | True | False |
| Clinical Context | Presenting complaint | History of Present Illness discussion | History of Present Illness discussion | Family History | Patient History | Patient History / in History of Present Illness discussion |
| PS Status |  |  |  | Father |  |  |
| Concept type | Disorder | Disorder | Disorder | Disorder | Procedure | Disorder |
| Specificity | High | High | Moderate | Moderate | Moderate | Low |
| Document score. | High | High | Moderate | Moderate | Low | Moderate |
|  |  | *Results of categorization* |  |  |  |  |
| Clinical Importance | High | High | Moderate | Low | Low | Moderate |

FIG. 9.

SEARCHING AN ELECTRONIC MEDICAL RECORD

BACKGROUND

Clinical facilities (e.g., hospital, therapy center, practice group) or other managers of medical information may maintain a patient's medical record in an electronic database. An individual patient's medical record is called an electronic medical record or personal health record. The electronic medical record may include electronic documents and database entries. Over time, a patient's electronic medical record may contain a lot of information. The information may be reached by browsing through the electronic medical record and opening documents to look for information. The large amount of information makes it difficult to find desired information.

SUMMARY

Embodiments of the invention are defined by the claims below, not this Summary. A high-level overview of various aspects of the invention are provided here for that reason, to provide an overview of the disclosure, and to introduce a selection of concepts that are further described below in the Detailed Description. This Summary is not intended to identify key features or essential features of the claimed subject matter, nor is it intended to be used as an aid in isolation to determine the scope of the claimed subject matter.

In a first aspect, one or more computer-storage media having computer-useable instructions embodied thereon for performing a method of finding information in an electronic medical record are provided. The method includes receiving a search query from a user to search the electronic medical record, wherein the electronic medical record is associated with a patient. The electronic medical record includes a plurality of electronic documents that describe a medical history for the patient and is stored on the computer-storage media. The method also includes identifying one or more components of the electronic medical record that contain text that matches the search query, wherein each of the one or more components is a section of text with in the electronic medical record that includes one or more words. The method also includes determining a query-responsiveness score for each of the one or more components that match the search query. The query-responsiveness score indicates how responsive an individual component is to the search query. The method further includes presenting search results that communicate information describing each of the one or more components. The search results are displayed ordered according to the query-responsiveness score assigned to each of the one or more components.

In a further aspect, one or more computer-storage media having computer-useable instructions embodied thereon for performing a method of searching an electronic medical record for a selected clinical concept are provided. The method includes receiving a search query that includes a clinical concept from a user. The clinical concept is an aspect related to a person's health. The method also includes identifying one or more uses of the clinical concept in the electronic medical record, wherein the electronic medical record is an electronic description of a medical history for a patient and is stored on the computer-storage media. The method further includes determining a query-responsiveness score for each document within the electronic medical record in which the clinical concept is used. The query-responsiveness score describes how important a particular document is likely to be to the user. The query-responsiveness score is determined based on a clinical-importance score for each of the one or more uses of the clinical concept and at least one boost factor that is based on the search query and the user. The method also includes presenting search results based on the query-responsiveness score associated with said each document within the electronic medical record in which the clinical concept is used.

In a further aspect, one or more computer-storage media having computer-useable instructions embodied thereon for performing a method of preparing an electronic medical record for electronic searching are provided. The method includes receiving the electronic medical record that includes information describing at least a portion of a medical history associated with a patient. The method also includes identifying clinical concepts within the electronic medical record, wherein the clinical concept is an aspect related to a person's health. The method also includes, for each of the clinical concepts, determining a patient-subject status for each use of the clinical concept in the electronic medical record, wherein the patient-subject status indicates whether the patient is a subject of a particular use of the clinical concept. The method further includes, for each of the clinical concepts, determining a truth status for each use of the clinical concept in the electronic medical record, wherein the truth status indicates whether the clinical concept was expressed positively, negatively, ambiguously, or unknown. The method further includes, for each of the clinical concepts, determining a clinical-usage context for each use of the clinical concept in the electronic medical record, wherein the clinical-usage context describes how the clinical concept was used in the electronic medical record. The method also includes, for each of the clinical concepts, determining a specificity factor for each use of the clinical concept in the electronic medical record based on the degree of specificity, precision or narrowness of scope of the concept, as derived from the concept's position in a clinical ontology, or other reference information. The method further includes assigning a clinical-importance score to each use of the clinical concept in the electronic medical record based on a the patient-subject status, the truth status, the clinical-usage context, and the specificity factor and storing the clinical-importance score associated with each use of the clinical concept in each document within the electronic medical record in a data store.

BRIEF DESCRIPTION OF THE SEVERAL VIEWS OF THE DRAWINGS

Illustrative embodiments of the present invention are described in detail below with reference to the attached drawing figures, wherein:

FIG. 7 is an illustrative screen display of search results that are responsive to a submitted clinical concept, in accordance with an exemplary embodiment of the present invention;

FIG. 8 illustrates the identification of clinical concepts in a document that is part of the electronic medical record, in accordance with an exemplary embodiment of the present invention; and FIG. 9 illustrates indexing clinical concepts and related information in an index, in accordance with an exemplary embodiment of the present invention.

DETAILED DESCRIPTION

Figure 1:
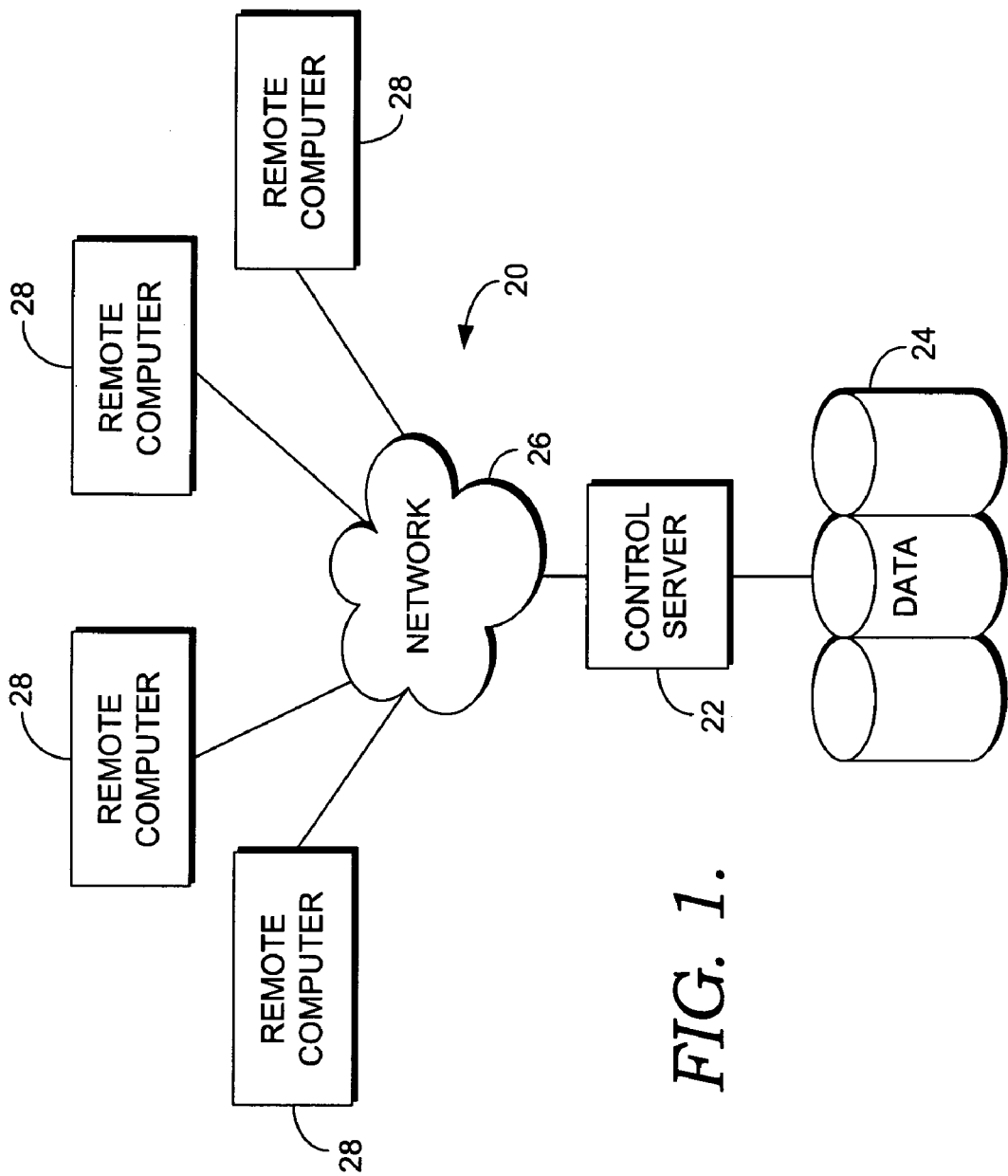
FIG. 1 is a block diagram depicting an exemplary computing environment suitable for use in implementing embodiments of the present invention.

Embodiments of the present invention allow a user to search for information in an electronic medical record ("EMR"). An EMR is a collection of information describing the medical history of a patient. The EMR may be managed by a variety of sources including a clinical facility, such as a hospital, and the patient. In one embodiment, the EMR is personal health record. The EMR for a single patient may contain combinations of database entries and electronic documents that are related to the patient's medical history. The database entries may be created by filling out an electronic form presented in a user interface. The documents and database entries may include encoded data that describes a portion of a patient's medical history. For example, a diagnosis for diabetes may be codified as "D234539A293" and recorded in a document or database entries. EMRs for groups of patients may be collected in a single data store.

Embodiments of the present invention allow a user to submit a search query through an interface and return search results that are responsive to the search query. As will be described in more detail subsequently, the search results may be ordered according to a query-responsiveness score so that the most important matching components of the EMR can be quickly located at the top of the result list. Search results may present components of the EMR at any level of granularity. A component of the EMR may be any text within the EMR including a document within the EMR or a section of text within a document (e.g., a paragraph, document section) in the EMR, or any structured and/or codified element of information contained within the EMR. For example, components may be documents within the EMR, a word within the EMR, a sentence within the EMR, a single use of a clinical concept within the EMR, or a component of a document within the EMR. Different embodiments evaluate components of the EMR and present search results based on those components at different levels of granularity. The analysis used to determine the responsiveness of a search result, which is described hereafter, may be performed at whatever level of granularity the search results are presented. Throughout this disclosure, the level of granularity will most commonly be described as a document in the EMR or a component of the EMR, but embodiments of the present invention are not intended to be limited to these descriptions. As will be pointed out subsequently, some of the factors used to determine the responsiveness of a search result may not be used when the search results are at a very low level of granularity, such as a single word or a single use of a clinical concept. In one embodiment, the search results are matched based on clinical concepts in the query and clinical concepts in components of the EMR. A clinical concept is an aspect related to a person's health. A clinical concept describes any aspect of a person's health condition, or any object, action, attribute or idea that is related to a health condition. Examples include: diseases; symptoms; clinical observations and findings; diagnostic tests; diagnostic or therapeutic procedures; organisms, substances, devices or products related to health conditions; anatomic structures including genomic; phenotypic expression; behavior, family and social context related to health conditions; risk factors and outcomes; facilities and care providers. For example, heart disease and a heart attack are examples of clinical concepts.

The search results are ordered according to a query-responsiveness score that is calculated for each matching search result (e.g. document, document portion). In one embodiment, the query-responsiveness score is calculated by combining a set of clinical-importance scores with a set of boost factors. The clinical-importance score measures how important the clinical concepts used within each specific component of the EMR are, apart from a query. In one embodiment, the clinical-importance score is generated for each use of a clinical concept within the EMR in advance and stored in an index.

There are at least two categories of boost factors that may be combined with the clinical-importance score to calculate the query-responsiveness score. Document-boost factors measure the responsiveness of a search-result (e.g., a document, a component of a document, a component of the EMR) without considering the query. Query-boost factors measure the document's responsiveness to the query using information related to the query, such as the role of the user submitting the query. The boost factors are assigned to produce a good fit between the query and the potential search result. One or more boost factors may be combined with the set of clinical-importance scores to generate a query-responsiveness score for the component of the EMR.

Having briefly described embodiments of the present invention, an exemplary operating environment suitable for use in implementing embodiments of the present invention is described below. Some of the wording and form of description is done to meet applicable statutory requirements. Although the terms "step" and/or "block" or "module" etc. might be used herein to connote different components of methods or systems employed, the terms should not be interpreted as implying any particular order among or between various steps herein disclosed unless and except when the order of individual steps is explicitly described.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, cellular telephones, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer-storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The control server 22 typically includes therein, or has access to, a variety of computer-readable media, for instance, database cluster 24. Computer-readable media can be any available media that may be accessed by control server 22, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer-storage media discussed above and illustrated in FIG. 1, including database cluster 24, provide storage of computer readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Many other internal components of the control server 22 and the remote computers 28 are not shown because such components and their interconnection are well known. Accordingly, additional details concerning the internal construction of the control server 22 and the remote computers 28 are not further disclosed herein.

Although methods and systems of embodiments of the present invention are described as being implemented in a WINDOWS or LINUX operating system, operating in conjunction with an Internet-based delivery system, one of ordinary skill in the art will recognize that the described methods and systems can be implemented in any system supporting the search of electronic medical records. As contemplated by the language above, the methods and systems of embodiments of the present invention may also be implemented on a stand-alone desktop, personal computer, cellular phone, smart phone, PDA, or any other computing device used in a healthcare environment or any of a number of other locations.

Figure 2:
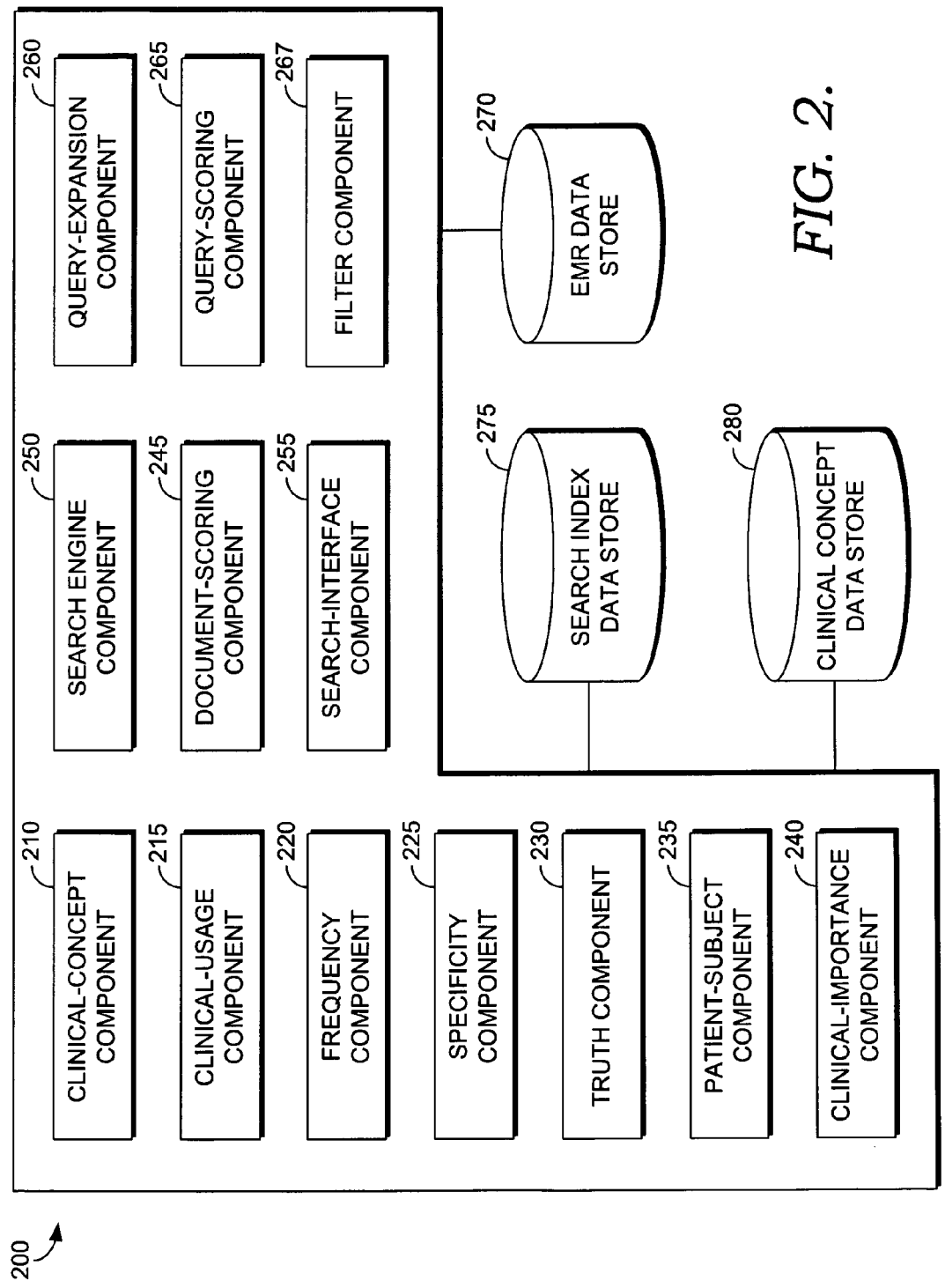
FIG. 2 is a block diagram depicting an exemplary computing architecture suitable for searching an electronic medical record for components that are responsive to a search query, in accordance with an embodiment of the present invention.

Turning now to FIG. 2, a block diagram is illustrated that shows an exemplary computing-system architecture 200 suitable for searching an electronic medical record for components that are responsive to a search query, in accordance with an embodiment of the present invention. The computing-system architecture 200 shown in FIG. 2 is merely an example of one suitable computing system and is not intended to suggest any limitation as to the scope of the use or functionality of the present invention. The computing system architecture 200 should not be interpreted as having any dependency or requirement related to any single component/module or combination of component/modules illustrated therein.

The components in computing-system architecture 200 work together to analyze and index an EMR and analyze a search query to provide a user with the search results that are most responsive the user's search query. Computing-system architecture 200 includes clinical-concept component 210, clinical-usage component 215, frequency component 220, specificity-factor component 225, truth component 230, patient-subject component 235, clinical-importance component 240, document-scoring component 245, search-engine component 250, search-interface component 255, query-expansion component 260, query-scoring component 265, EMR data store 270, search-index data store 275, and clinical-concept data store 280. Computing-system architecture 200 may operate in a single computing device, such as control server 22 shown in FIG. 1. In the alternative, computing-system architecture 200 may operate in a distributed computing environment that includes multiple computing devices coupled with one another via one or more networks. Such networks may include, without limitation, one or more local area networks (LANs) and/or one or more wide area networks (WANs). Such network environments are commonplace in offices, enterprise/wide computer networks, intranets, and the Internet. Accordingly, the network, or combination of networks, is not further described herein.

Clinical-concept component 210 may identify clinical concepts within a search query and components of an EMR. The clinical-concept component 210 may interact with the clinical-concept data store 280 in order to identify clinical components. The clinical-concept data store 280 contains at least one clinical-concept nomenclature and may contain several. A clinical-concept nomenclature is a vocabulary of medical terminology. A vocabulary contains terms and expressions related to a specific domain. Clinical nomenclatures may describe conditions, symptoms, diagnostic procedures, organisms, substances, treatments and other clinically relevant concepts. The data store 280 may also contain local, non-clinical concepts such as facilities, locations, care providers. A clinical-concept ontology may contain information about the attributes and relations of the terms in a clinical-concept nomenclature. At the simplest level, the clinical-concept ontology organizes terms around clinical concepts, and relates "synonyms" or terms that describe the same concept. For example, the terms "heart attack" and "myocardial infarction" describe the same clinical concept, and can be related as synonyms. The ontology can also contain more complex relationships. Specificity is expressed as a hierarchy of "is-a" relationships. For example, the concept described as "left main coronary artery disease" can be related to the more general concept of "heart disease," of which it "is a" specific form. Additional relations depend on the nature of the clinical-concept ontology. They can include relations that link disease with similar causes, a disease to a symptom that it causes, a medication to the disease it treats, and many more. In one embodiment, SNOMED CT (Systematized Nomenclature of Medicine-Clinical Terms) is used as the clinical-concept ontology. SNOMED CT is a systematically organized, computer-processable collection of medical terminology.

Clinical-concept component 210 may identify each of the clinical concepts within an electronic medical record. The clinical concepts may be identified by performing a textual analysis on the EMR and matching phrases to clinical concepts within a clinical-concept ontology. Clinical concepts may also be identified by mapping codified data in the EMR to the clinical-concept ontology. For example, the codified data describing a diagnosis may be mapped to the clinical concept describing the diagnosis. Once identified, the clinical concepts within the EMR may be stored in an index used for searching the electronic medical record. Additional information describing the use and context of the clinical concept within the EMR may also be indexed. The additional information may be provided by other components. The function of those components is described subsequently. In one embodiment, each use of a clinical concept is indexed according to the document or component of the EMR in which the clinical concept is used.

The clinical-concept component 210 may also identify clinical concepts within the search query using a similar methodology. The clinical concepts identified in the search query may be communicated to the search-engine component 250. Clinical-concept component 210 may expand a specific clinical-concept found in the search query by traversing the clinical-concept ontology to find more general, more specific, and/or sibling clinical concepts. The expanded set of clinical concepts may be used to expand the search criteria and/or to expand the information indexed that describes a particular document or component in the EMR. For example, the primary clinical concept identified in the search query and expanded clinical concepts may be used to identify matching clinical concepts in an index. Additionally, expanded clinical concepts may be indexed along with the primary clinical concept used in the documents or components in the EMR.

Clinical-usage component 215 performs part of an analysis that is used to determine the importance of a particular use of a clinical concept within an EMR. The clinical-usage component 215 ascertains the context or role in which a clinical concept is used the EMR. The particular use of a clinical concept may be assigned a pre-defined clinical-context category. The clinical-usage context may be determined by ascertaining in what part of a document the clinical concept is used, or how the clinical concept is used in certain sentences. Examples of clinical-usage contexts include: the presenting complaint, patient history, family history, review of systems, physical exam, prescription, order, lab result, vital sign, diagnosis, procedure, and others. This list of clinical-usage contexts is not meant to be exhaustive.

The clinical-usage component 215 may perform natural language processing and grammatical analysis to determine the clinical-usage context. Document metadata may also be analyzed to determine what role a portion of a document or a sentence in a document plays in the electronic medical record. Other markers and headings included within the EMR or within documents that are within the EMR may be used to help identify the clinical-usage context. The clinical-usage context may be stored in an index, such as the index in search-index data store 275, along with the use of the associated clinical concept. The clinical-usage context may be used as a factor in assigning a clinical-importance score to a particular use of a clinical concept. The determination of a clinical-importance score is described in more detail subsequently.

The frequency component 220 analyzes the frequency with which a clinical concept occurs within an electronic medical record. The frequency component 220 may assign a frequency score to each use of a clinical concept. In one embodiment, the frequency score is the result of a calculation. For example, the number of uses of a particular-clinical concept in an EMR divided by the number of uses of all clinical concepts in the EMR. Clinical concepts that occur alone in a document may be less important than clinical concepts that occur multiple times in a document. In other words, multiple appearances of the same or related clinical concepts within a document may indicate that the clinical concept is a main subject of the document. A clinical concept that occurs rarely across multiple electronic medical records may have more importance than common clinical concepts. In one embodiment, two frequencies scores are calculated. The first frequency score is based on occurrences of the clinical concept within a document in the EMR and the second score is based on the number of occurrences of the clinical concept within the entire EMR or across multiple EMRs. The actual frequency score or a frequency rank may be stored in an index with the associated the use of the clinical concept. The frequency score may be used to determine a clinical-importance score for the use of the clinical concept.

The specificity component 225 determines the specificity factor of a clinical concept based on the degree of specificity, precision or narrowness of scope of the concept, as derived from the concept's position in a clinical ontology, or other reference information. The specificity factor represents the precision, or degree of detail of a clinical concept. For example, "heart disease" is a general, or a fairly non-precise concept, whereas "right coronary artery occlusion" (a form of heart disease) is a precise concept. The specificity factor is a powerful tool for ranking and evaluation because precise clinical concepts tend to be more clinically interesting and significant, and also because the documents that describe concepts in very precise language are usually the documents that contain the most clinically interesting information about that concept. The specificity factor may be derived from a combination of the concept relations in a clinical-concept ontology, and additional content and algorithms. The specificity factor may be expressed as a numeric level within a hierarchy. Alternatively, the specificity factor may be expressed as a category. For example, the most general clinical concepts may be designated with a specificity factor of "1" or as "low" specificity. More precise concepts could be grouped as medium or high. The specificity factor may be indexed in association with each use of the clinical concept. The specificity factor may be used as an additional factor to determine a clinical-importance score for the clinical concept.

The truth component 230 performs a grammatical analysis to assign a truth status to a use of a clinical concept. The truth status indicates whether the use of the clinical concept is positive, negative, ambiguous, or unknown. For example, the phrase "the patient complained of chest pain" would create a positive truth status for to the clinical concept "chest pain." On the other hand, the phrase "the patient denies chest pain" would warrant a negative truth status for "chest pain" because the patient said he had not had chest pain. The truth status may be stored in an index in association with the particular use of the clinical concept. The truth status may be used to determine an importance score for a particular use of the clinical concept. A negative truth status may make a use of a clinical concept less important. A positive truth status may increase the importance score calculated for the particular use of the clinical concept.

The patient-subject component 235 determines the patient-subject status of a use of a clinical concept. The patient-subject status indicates whether the patient is the subject being described by the clinical concept. For example, a medical history indicating the patient's father died of cancer would not have the patient as the subject of the clinical concept "cancer" and the patient-subject status would be false. On the other hand, the patient is the subject of the clinical concept "chest pain" in a reference to the patient complaining of chest pain in a presenting complaint. In this case, the patient-subject status would be true. The clinical subject may be stored in an index in association with the particular use of the clinical concept. The patient-subject status may be used as an additional factor to determine a clinical-importance score for the use of the clinical concept.

The clinical-importance component 240 assigns a clinical-importance score to each use of a clinical concept within the electronic medical record. A use of a clinical concept is a single occurrence of the clinical concept within the EMR. A single clinical concept may be used multiple times within a single document within the EMR as well as within other documents in the EMR. Each use of a clinical concept may be assigned a clinical-importance score. The purpose of the clinical-importance score is to quantify how important a particular use of a clinical concept is likely to be to a person searching for components of the EMR in which the clinical concept is used. The more important the use, the more likely the document containing the use is interesting to the person submitting the search query. However, the clinical-importance score is calculated based on the use of a clinical concept within the EMR and without reference to any specific search query.

The clinical-importance score may be calculated based on several factors. Different embodiments of the present invention combine different factors to calculate each clinical-importance score. It may not be necessary to use every factor explained herein to calculate the clinical-importance score. Further, different weights may be given to different factors when calculating the clinical-importance score. Embodiments of the present invention are not limited to the specific examples given. In one embodiment, the clinical-importance score is calculated based on the clinical-usage context, the truth status, the patient-subject status, the specificity factor, and the frequency associated with the particular use of the clinical concept in this document compared to other matching documents in the patient's EMR. In another embodiment, the clinical-importance score is calculated based on the truth status, the patient-subject status, and the clinical-usage context. In another embodiment, the clinical-importance score is calculated based only on the clinical-usage context.

As stated previously, different weighting may be given to the different factors used to calculate the clinical-importance score. Regardless of the weight given to a factor in a particular embodiment, in general, the factors may increase or decrease the ultimate score as explained subsequently. When the patient is the subject of the use of the clinical concept, the importance score may be increased. A negative truth status for a use of a clinical concept may lower the importance score.

The importance score may be raised if the clinical-usage context is in a category that is authoritative and related to the patient. For example, if the clinical-usage context is the presenting complaint or the patient history, the importance score could be raised more than if the clinical-usage context is a patient's family history, since the family history is less directly related to the patient. Different categories of clinical-usage context may be given different values to plug into the calculation of the clinical-importance score. In general, the more closely the clinical concept is related to the patient and the more authoritative, the higher the importance score will be. A relatively high frequency of occurrence in a document within the EMR compared to other documents may increase the importance score because the clinical concept is more likely to be the subject of the document, and thus, more important than a clinical concept that may be mentioned tangentially or that is used indiscriminately in many documents.

Document-analysis component 245 gathers attributes describing components of the electronic medical record. In one embodiment, the components of the EMR are analyzed at the document level of granularity. A component of the EMR may contain multiple uses of one or more clinical concepts. The document or component attributes may be stored in the index and used to calculate document-boost factors that increase a responsiveness rank of a matching component within the search results.

In addition to collecting document attributes, the document-analysis component 245 may also assigns each document one or more primary-focus domains and one or more generic-document domains. For example, the primary-focus domain may be "physician" for a particular document authored by a physician. Other examples of primary-focus domains include "nurse-focused" and "social-worker-focused." The primary-focus domain and the generic-domain may be used for calculating boost factors. The generic-document domains may include a designation that the document is a clinical document, lab result, vital sign, problem, order, or other clinical event. The primary-focus domain and generic-documents domains may be stored in an index.

Many different attributes and collections of attributes may be used to calculate document-boost factors. Document-boost factors include a source-boost factor, a class-boost factor, and a document-type-boost factor. A source-boost factor may be calculated based on the source of a document. The source-boost factor may be increased or decreased according to the importance of the source of the document. For example, the source-boost factor may be increased if the document is a primary source, such as a discrete lab result in contrast to a secondary source, such an end-of-the-day summary that repeats the lab result. In addition to the source-boost factor, a class-boost factor may be used. The class-boost factor is based on the importance of a document as determined by the importance of the class of which the document is a part. The class-boost factor may be increased if the document class is a "clinician-authored document." In contrast, the class-boost factor may be lowered if the document class is "a procedure note," or is authored by a non-clinician. In addition to the class-boost factor and source-boost factor, the document type may be considered when calculating a document-type-boost factor. For example, the document-type-boost factor may be increased if the document is a discharge summary or transfer summary. Both the discharge summary and transfer summary tend to be more important because they contain authoritative summaries of a patient's progress. Similarly, an admission note may be more important because it may define the cause of a new episode. Daily progress notes, medical student notes, chart abstractor notes, and other notes may be less important and would tend to decrease the boost factor.

The domains may also be incorporated into document-boost factors or query-boost factors that are used as part of the calculation of the query-responsiveness score. For example, the domains may be used in combination with information related to the query to calculate a role-boost factor. The role-boost factor is based on matching a search query submitted by a particular category of clinician (e.g., nurse, doctor, social worker) to a document associated with the same category of clinician. For example, if the search query is submitted by a nurse, then the document's query-responsiveness score may be increased, through a boost factor, if the primary-focus domain is nurse. Similarly, if a search query is entered by a social worker, then the query-responsiveness score may be increased if the primary focus of the document is social worker.

Search-engine component 250 receives a search query and retrieves documents or components of documents from the electronic medical record that are responsive to the search query. A document or component of a document is responsive to the search query when a portion of the document or component of a document matches the search query or an expansion of the search query. Search-engine component 250 may use the search index in search-index data store 275 to find search results. The search results may be presented in an order intended to present the most responsive results first. The most responsive results may be determined using a query-responsiveness score (to be discussed subsequently). The search-engine component 250 may present search results that describe component of an EMR, a document in an EMR, or a component of a document in the EMR. A component of a document may be one or more words within the document.

Figure 6:
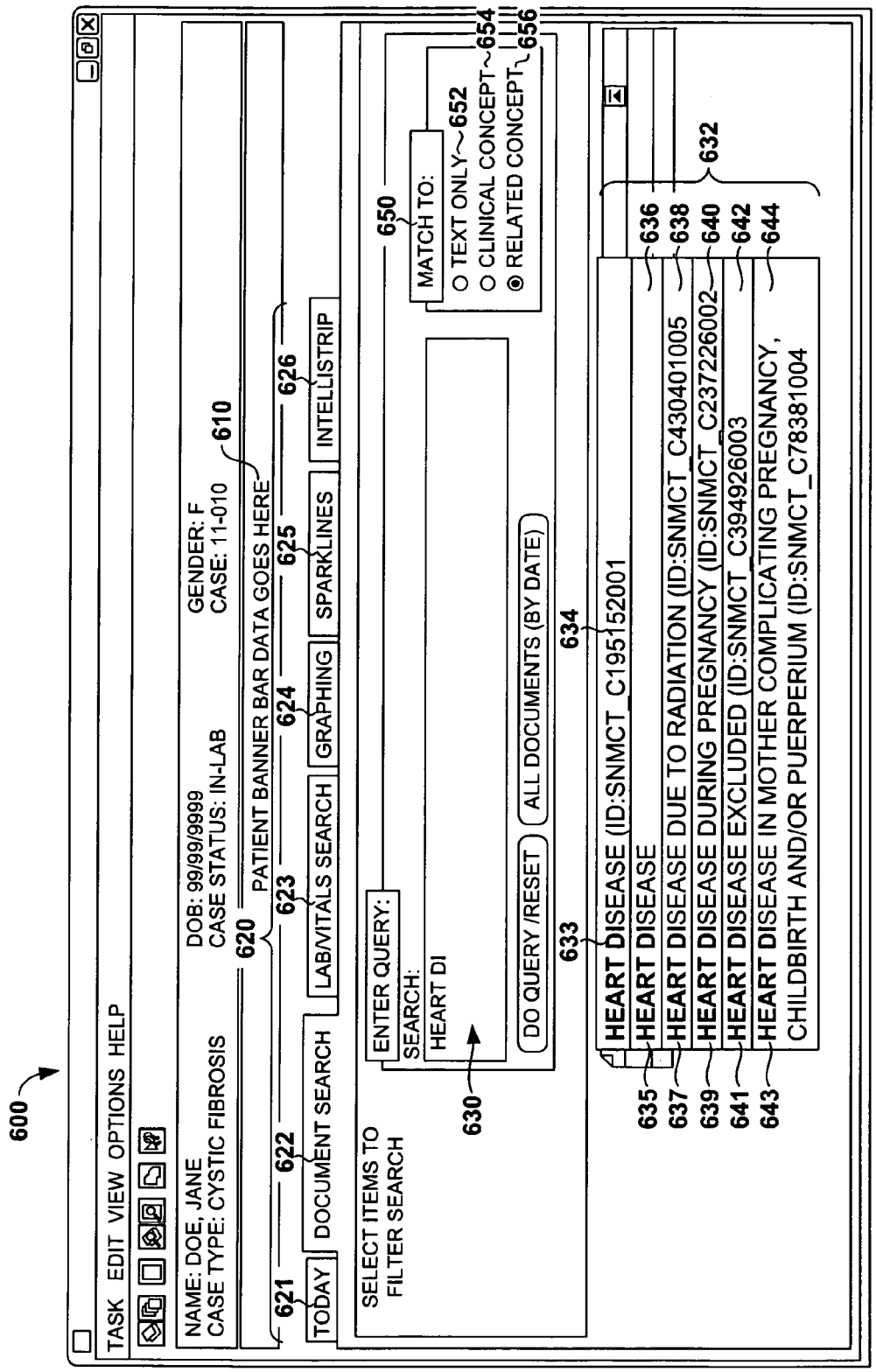
FIG. 6 is an illustrative screen display of an interface to receive a search query, in accordance with an exemplary embodiment of the present invention.
Figure 7:
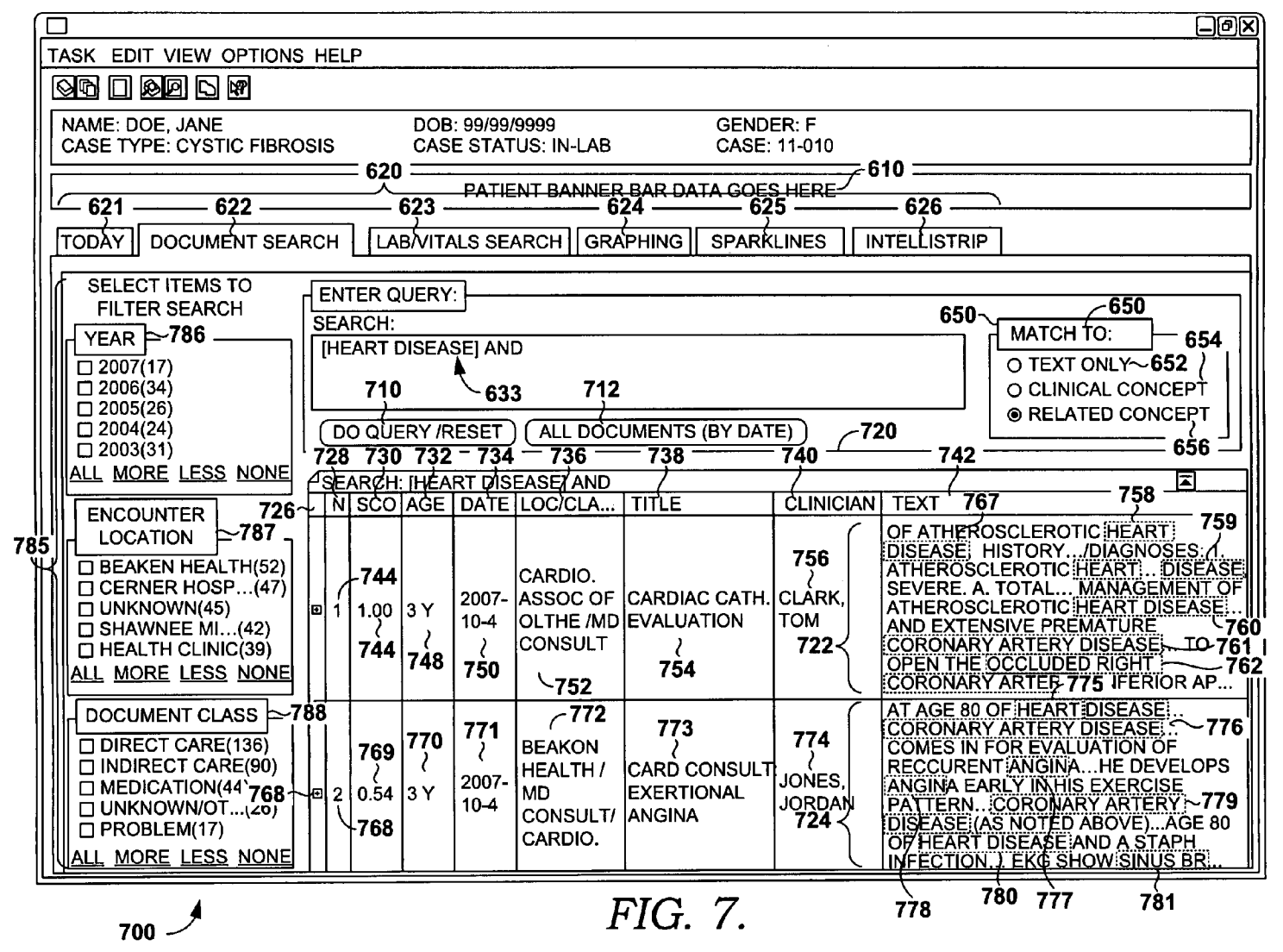

Search-interface component 255 presents a graphical user interface to a user for receiving search criteria and presenting search results. An example of a graphical user interface is shown in FIGS. 6 and 7. These figures will be described in more detail subsequently. In addition, the search-interface component 255 may also present filter options.

Query-expansion component 260 expands the search query to create a plurality of expanded search terms. The plurality of expanded search terms are used by the search-engine component 250 to find and rank additional search results. The degree of expansion performed by the query-expansion component 260 may differ depending on the search mode selected. For example, in a text only search mode, the query-expansion component 260 may be limited to only stemming each word within the search query. Stemming a word reduces the word to its root. For example, the stem of "dogs" is "dog," and the stem of "changing" is "change." Query-expansion component 260 may, in conjunction with other components, expand terms in the search query. For example, the plurality of expanded search terms may include medical synonyms of words submitted in the search query. In addition, clinical concepts identified within the search query may be expanded to include sibling, child, and/or related clinical concepts from the clinical-concept ontology. The query-expansion component 260 may transmit the search terms and expanded search terms to the search-engine component 250.

Query-scoring component 265 assigns a query-responsiveness score to each search result returned in response to a search query. As described previously, a search result may be any component of the EMR, including a document or a part of a document. For the sake of simplicity, the calculation of a query-responsiveness score will be described using a document as a search result. However, a query-responsiveness score may be calculated for any portion of the EMR for which the necessary information is available. The search results may be received from the search-engine component 250.

The query-responsiveness score for an individual document matching the query may be calculated by combining the clinical-importance scores assigned to each use of a clinical concept in the individual document with one or more document-boost factors and query-boost factors. The query-scoring component 265 may calculate one or more boost factors including the closeness-boost factor.

A closeness-boost factor may be calculated for each matching combination of clinical concepts when the primary clinical concept in the query is expanded. A matching combination of clinical concepts includes a clinical concept related to the query and a use of the same clinical concept in the particular document. The clinical concept related to the query may be the primary clinical concept and/or expanded clinical concepts. The closeness-boost factor may be used to increase the query-responsiveness score for combinations including the primary clinical concept and expanded clinical concepts that are close to the primary clinical concept. Since a user's query may be exploded into a set of synonyms, child, and related concepts, in one embodiment, the closeness-boost factors are assigned to combinations with the primary clinical concept and to combinations with the expanded clinical concepts such that combinations with the primary clinical concept have the most importance, and combinations with the more distant 'related' concepts have less importance. In general, the closer on the clinical-concept ontology the expanded clinical concept is to the primary (e.g. original) clinical concept, the higher the closeness-boost factor. In contrast, the further away on the clinical-concept ontology that the expanded clinical concept is, the lower the boost factor. The closeness-boost factors are combined with the clinical-importance scores to determine the query-responsiveness score of the document or component. For example, a document including a clinical concept with a high clinical-importance score matching to an expanded clinical concept that is a sibling of (i.e., close to) the primary clinical-concept would receive a higher query-responsiveness score than when the same clinical concept is combined with an expanded clinical concept several layers away from the primary clinical concept. A boost factor based on the closeness of the clinical concept from the query is only used when the query is expanded. Other boost factors may be used to calculate into the query-responsiveness score when the query is not expanded or in combination with the closeness-boost factor given combinations of the primary-clinical concept and closely related expanded-clinical concepts.

In addition to the closeness-boost factor, additional boost factors may be used based on other document and/or query attributes. For example, a role-boost factor based on the role to the person submitting the query and the role of the person associated with a component of the EMR may be used. The role-boost factor may be calculated by the query-scoring component 265. The role-boost factor may be increased for a document with a primary-focus domain of "nurse" when the query is submitted by a nurse. Similarly, the class-boost factor used. As described previously, the class-boost is based on the importance of a document-class. For example, the class-boost factor may be higher if the document class is "physician authored" and lower if the document class is "medical-student authored." In another embodiment, a boost factor is time weighted. The time-weighted-boost factor increases for documents that are more recent. In yet another embodiment, the clinical-facility-boost factor increases if the document was generated in the same clinical facility as the one from which the query is submitted. Additional boost factors may be calculated based on one of more of the previously described attributes. All of the previously described boost factors may be combined, but not all boost factors need be used to calculate a query-responsiveness score. A query-responsiveness score may be calculated using just one, or none, of the previously described boost factors.

The Filter component 267 allows the user to filter the search results according to suggested or submitted criteria. For example, the filter component may provide an interface allows the user to filter search results according to date, document class, clinical facility, and the document's primary focus. In one embodiment, the filter component 267 suggests a filter criteria for the user to select along with an indication of how many of the search results match the filtered criteria. For example, the interface could indicate that 20 search results are in the document class "physician authored." In one embodiment, the search results may be filtered by clinical concepts found within the search results. Related clinical concepts may be aggregated into a general filter option that would present search results that include any of the related clinical concepts. The filter options could be presented with the clinical concepts having the highest aggregation of clinical-importance scores. These filter examples are not meant to be exhaustive, other filters based on factors store in the index are within the scope of this disclosure.

The Electronic medical record data store 270 contains the electronic medical records for one or more patients. An EMR is a collection of information describing the medical history of a patient. In addition, the EMR data store 270 may include electronic medical records from one or more clinical facilities. The EMR data store 270 may be accessed by other components within computing-system architecture 200.

Search-index data store 275 includes a search index which stores the words and the clinical concepts extracted from the patient's documents as described above. The search index may be isolated on a per patient or per clinical facility basis. In other embodiments, multiple patients and even multiple EMRs may be searched concurrently.

Clinical concept data store 280 contains one or more clinical-concept ontologies as described previously. In one embodiment, the clinical-concept ontology is based on a combination of SNOMED CT (to represent clinical conditions, symptoms, therapy, organisms, etc.) and RxNorm (to represent medications). Embodiments of the present invention are not limited to using SNOMED CT. Other hierarchies of medical terminology may be used.

Figure 3:
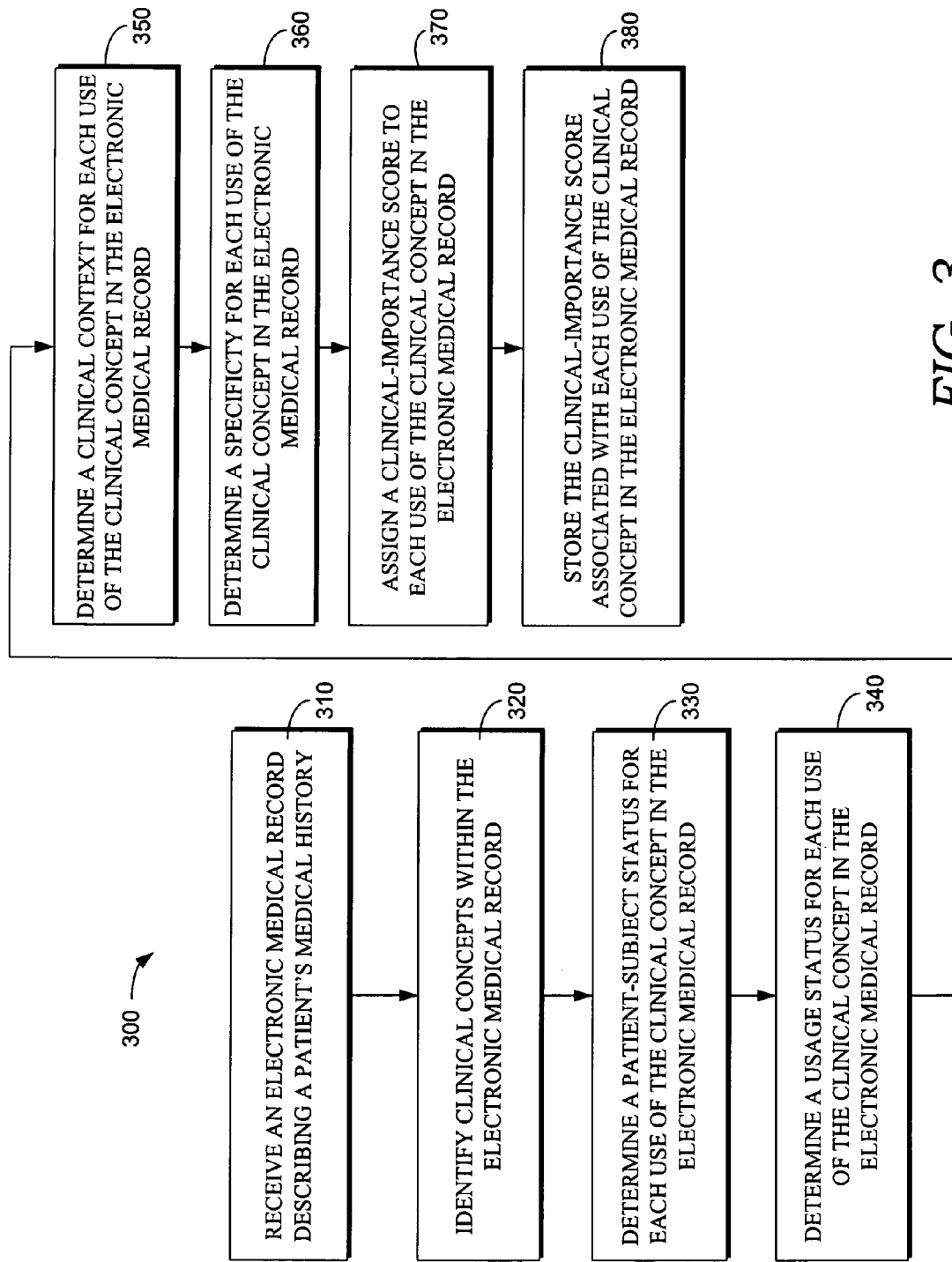
FIG. 3 is a flow diagram showing a method of preparing electronic medical records for electronic searching, in accordance with an embodiment of the present invention.

Turning now to FIG. 3, a method 300 of preparing electronic medical records for electronic searching is provided, in accordance with an embodiment of the present invention. At step 310, an electronic medical record that includes information describing at least a portion of a medical history associated with a patient is received. As described previously, an electronic medical record includes information that describes a patient's medical conditions, treatments received, and other medical information for the patient. The EMR may be recorded by clinicians, the patient, or others. Electronic medical records may be generated by a single clinical facility or by multiple clinical facilities. The electronic medical record may be stored in a data store that is accessible to a single clinical facility or to multiple clinical facilities.

In one embodiment, any information in the electronic medical record that is not already formatted as an displayable document is converted into a new displayable document. The electronic medical record may contain structured and/or codified data including database entries. In one embodiment of the present invention, the database entries are converted into electronic documents. The converted electronic documents include entries from the database fields and descriptions of the database fields. Thus, once non-document portions are formatted, an electronic medical record may consist of a plurality of electronic documents that are displayable by a search engine as a search result. In one embodiment, the newly created electronic documents may be used as component of the EMR to associate with boost factors.

At step 320, clinical concepts in the electronic medical record are identified. A clinical concept describes any aspect of a person's health condition, or any object, action, attribute or idea that is related to a health condition. Examples include: diseases; symptoms; clinical observations and findings; diagnostic tests; diagnostic or therapeutic procedures; organisms, substances, devices or products related to health conditions; anatomic structures including genomic; phenotypic expression; behavior, family and social context related to health conditions; risk factors and outcomes; facilities and care providers. For example, heart disease and a heart attack are examples of clinical concepts.

The identification of clinical concepts in a document that is part of an electronic medical record is illustrated in FIG. 8. For the sake of clarity, only a few of the clinical concepts and significant words are shown. The electronic document 800 in FIG. 8 is a summary of a patient's visit to a doctor's office. The electronic document 800 includes a document type 810. The document type 810 field is a description of what category the electronic document is in. In this case, the document type 810 is an office visit. The document date 812 is Oct. 4, 2005. The document title 814 is "Mr. X., pepperoni pizza with hot peppers." The document author 816 is "T. Jones, M.D." The document source 818 is "River Heights Medical Association." These document attributes may be associated with each word or use of a clinical concept within the document. These document attributes may also be included as document metadata. Factors, such as the clinical-usage context may be determined using these factors.

The words in electronic document 800 that are in blocks may be clinical concepts. The blocked words include "peppers" 820, "heartburn" 822, "peppers" 824, "heartburn" 825, "heart attack" 826, "G.I. ulcer" 828, "abdominal hernia repair" 830, and "heart disease" 832. These words may be selected based on analysis that looks for medical terms, keywords and other words/terms of interest.

Returning now to FIG. 3, at step 330, a patient-subject status for each use of a clinical concept of the electronic medical record is determined. The patient-subject status indicates whether the patient is the subject of the clinical concept. For example, the patient is the object of the sentence "he has never been diagnosed with a G.I. ulcer" in electronic document 800. The patient-subject status may be determined using a grammatical analysis of text in which the clinical concept occurs. Each instance of a clinical concept may be associated with a different patient-subject status. The patient-subject status may be recorded as true\false. True indicates that the patient is the subject of the clinical concept. In another embodiment, the patient-subject status may be recorded with the name of the subject associated with the clinical concept. For example, the patient-subject status may be recorded as "patient's father."

At step 340, a truth status of the particular-clinical concept is determined. The truth status indicates whether the clinical concept was expressed positively, negatively, ambiguously, or unknown. For example, referring to electronic document 800 "the worst heart burn I ever had, so bad I thought I was having a heart attack," refers positively to heartburn and ambiguously to heart attack. In this example, the truth status could be recorded as positive for both heartburn and ambiguous for heart attack.

At step 350, a clinical-usage context of each clinical concept is determined. The clinical-usage context describes how the clinical concept was used in electronic medical record. The clinical-usage context may be determined based on the section of the electronic document in which the use of the clinical concepts occurs or by analysis of the grammar of the sentence in which the concept is used. The clinical-usage context may also be determined based on the type of document in which the use of the clinical concept occurs. For example, "heartburn" 825 in electronic document 800 is in the clinical-usage context of the presenting complaint. "Abdominal hernia repair" 830 in electronic document 800 is in the clinical-usage context of a patient medical history. Each clinical concept may be categorized into one or more of a predefined group of clinical-context categories. Examples of clinical-usage contexts include a presenting complaint section, a patient history, a family history, a review of systems section, a physical exam record, a prescription, order, a lab result, a vital sign, a diagnosis, and a procedure record.

At step 360, a specificity factor is determined for the particular-clinical concept based on the degree of specificity, precision or narrowness of scope of the concept, as derived from the concept's position in a clinical ontology, or other reference information. As described previously, the clinical-concept ontology describes relationships between clinical concepts. The specificity factor could be recorded as a group category, such as high medium, or low. The specificity factor could also be recorded as a level in the clinical-concept ontology.

In one embodiment, a document-importance factor is determined for the particular use of the clinical concept. The document importance is the relevance of the particular-clinical concept to the main subject of the document. This is determined by clustering the clinical concepts in the document into clinical categories. In the case of diseases and symptoms, the cluster of related concepts would correspond to body-system-condition categories. The frequency of references to each category is evaluated to determine the "subject(s)" or areas of focus of the document. Weighting is also applied based on the clinical usage of the concepts. For example, consider two documents that each contain one use of the concept "heart disease." One document also contains many concepts related to heart disease, such as the diagnostic test "echocardiogram," the medication therapy "statin," and the clinical finding "S-T segment depression." In addition, the therapeutic intervention "cardiac catheterization" is contained in the significant clinical usage of "assessment and plan." In the second document, "heart disease" is also mentioned, but without any closely related concepts. The "document importance" of the concept "heart disease" is high in the first instance, low in the second.

At step 370, a clinical-importance score is computed and assigned to each clinical concept. The clinical-importance score may be determined based on the patient-subject status of the particular-clinical concept, the truth status of the particular-clinical concept, the clinical-usage context of the particular-clinical concept, and the specificity factor of the particular-clinical concept. The various factors may be combined and given different weights to arrive at the clinical-important score. In other embodiments of the present invention, additional factors are used to calculate the clinical-important score. For example, as described in FIG. 2, the frequency of a particular-clinical concept within the electronic medical record or a plurality of electronic medical records may be used.

At step 380, the clinical-importance score associated with each clinical concept is stored in the document index. The index may store a clinical-importance score for each use of a clinical concept in association with the document in which each clinical concept is used. In another embodiment, the index may store a clinical-importance score for each use of a clinical concept in association with a component of the EMR in which each clinical concept is used. The storage of clinical-important scores in a searchable index is illustrated by FIG. 9. The index 900 in FIG. 9 includes text 910 from electronic document 800 shown in FIG. 8. The first row of text 910 includes "heartburn" 822, "heartburn" 825, "heart attack" 826, "heart attack" 828, "abdominal hernia repair" 830, and "G.I. ulcer" 832. Words such as "pepper" 820 are not included in the concept index because they are not associated with clinical concepts, thought they may be stored in an ordinary "word" index so that they can help refine searches for subjects that aren't clinical concepts. The next row lists the clinical concept 912 with which the word is associated. For example the word "heartburn" 822 is associated with clinical concept "heartburn" 913. Similarly "heartburn" 825 is associated with "heartburn" 914. Both "heartburn" 913 and "heartburn" 914 have the same SNOMED CT code. As described previously, the SNOMED CT is a hierarchy of medical terminology. Embodiments of the present invention are not limited to using the SNOMED CT medical hierarchy. Because each use of a clinical concept within the electronic medical record may be indexed, the same clinical concept may be indexed several times. The scores given to each use of a clinical concept may be different.

Continuing with FIG. 9, clinical concepts 912 include "myocardial infarction" 915, "myocardial infarction" 916, "repair of hernia of abdominal wall" 917, and "gastrointestinal ulcer" 918. Each clinical concept includes a series of attributes that are determined as described previously. The truth status 920, clinical-usage context 930, patient-subject status 940, clinical concept type 950, specificity factor 960, and document importance 970 are all recorded. Finally, the clinical-importance score 980 for each clinical concept is recorded. In the embodiment shown in FIG. 9, the clinical-importance score is summarized as a category of high, medium, or low. In another embodiment, the clinical-importance score could be recorded as a numerical value that is the result of a calculation.

Figure 4:
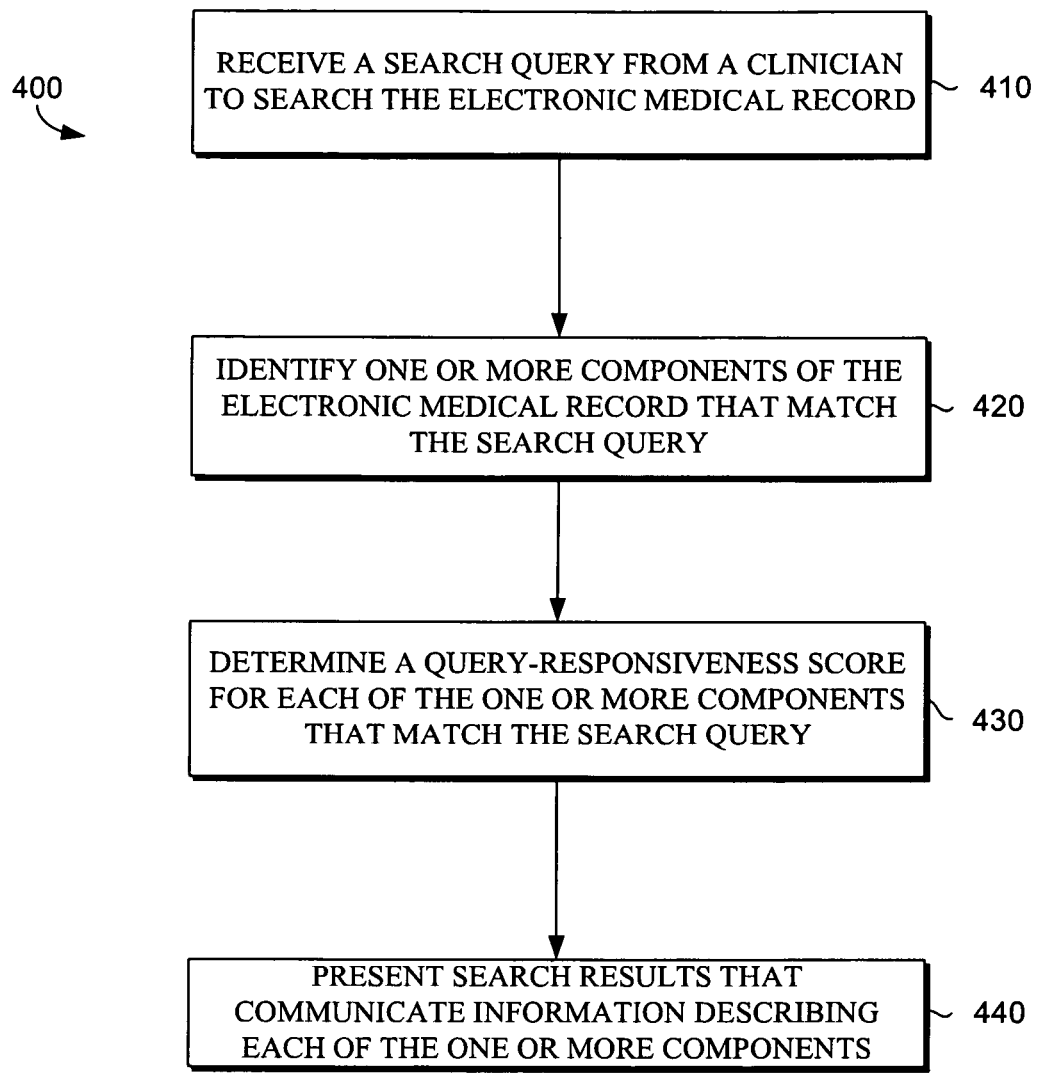
FIG. 4 is a flow diagram showing a method of finding information in electronic medical record, in accordance with an embodiment of the present invention.

Turning now to FIG. 4, a method 400 of finding information in electronic medical record is shown, in accordance with an embodiment of the present invention. At step 410, a search query is received from a clinician. An interface to receive a search query is illustrated in FIG. 6. The search interface 600 includes a patient-banner bar 610 to display identification information for the patient whose electronic medical record is being searched. The tab section 620 allows a clinician to navigate to various functions of the search interface 600. Several tabs are includes in the tab section 620. The tab section 620 includes a today tab 621, a documents search tab 622, a lab\vitals search tab 623, a graphing tab 624, a spark lines tab 625, and an IntelliStrip tab 626. The documents search tab 622 is shown as selected in FIG. 6. The search interface 600 includes a search input area 630. In an embodiment of the present invention, a list of suggested clinical concepts 632 is presented in response to entering a partial search query 631. Each suggested clinical concept includes the name of the clinical concept and the SNOMED CT identification number. The clinical concept "heart disease" 633 is paired with ID number 634. The clinical concept "heart disease due to ionizing radiation" 635 is paired with ID number 636. The clinical concept "heart disease due to radiation" 637 is paired with ID number 638. The clinical concept "heart disease during pregnancy" 639 is paired with ID number 640. The clinical concept "heart disease excluded" 641 is paired with ID number 642. The clinical concept "heart disease in mother complicating pregnancy, childbirth and/or puerperium" is paired with ID number 644. The start of each clinical concept begins with "heart di." the list of suggested clinical concepts 632 will show fewer clinical concepts as additional letters are typed into search input area 630.

Returning to FIG. 4, at step 420, one or more components of the electronic medical record that match the search query are identified. A component is a section of text including one or more words/terms. Embodiments of the present invention allow a user to specify the type of match required to return a search result. For example the user may select a text-only match. With a text-only match, stems of words in the search query must match stems of words within the electronic medical record to generate a search result. In another embodiment, the query terms are expanded to include medical synonyms of the query terms. The medical synonyms are used as additional query terms to match components of an electronic medical record to generate a search result. For example, "heart attack" and "myocardial infarction" may be medical synonyms. A search result would be identified if either "heart attack" or "myocardial infarction" were found in the electronic medical record. In another embodiment, the user may request matches based on "child" clinical concepts. At query time, the clinical concept identified in the search query would be expanded to include "children" of the base concept as defined by the associated clinical-hierarchy. These child concepts would also be used to match clinical concepts identified within the electronic medical record to produce a search result. In another embodiment, the user may search based on related concepts. With the related concepts choice, the original query term is expanded to include additional related clinical concepts which may be matched to documents in the patient's electronic medical record. The text-only matching option should return the least results and the related-concepts option should return the most results.

FIG. 6 illustrates an interface 600 for the user to select the matching criteria. The matching interface includes a text-only mode 652, a clinical concept mode 654, and related concepts mode 656. In one embodiment, the search results are dynamically updated as the user toggles between different matching criteria.

Returning to FIG. 4, at step 430, a query-responsiveness score is determined for each of the one or more components that match the search query. The query-responsiveness score indicates how responsive the individual component is to the search query. As described previously, the query-responsiveness score may be calculated based on a combination of the clinical-importance score of the matching clinical concepts with the one or more components and the associated boost factors, as described above. The calculation of a clinical-importance score and the various factors that may be considered when calculating the clinical-importance score have been described previously. Similarly, determining the boost factors has also been described previously.

At step 440, search results that communicate information describing each of the one or more matching components are displayed. As described previously, the matching components may be documents, portions of documents, or other portions of the EMR. The search results are displayed ordered according to the query-responsiveness score assigned to each of the one or more components.

FIG. 7 illustrates the display of search results that are responsive to a submitted clinical concept. Result interface 700 includes a search result display area 720. The search results display area 720 includes two search results, both of which are documents. Though not shown in FIG. 7, the search results may be components of a document. Each search result is displayed with an expansion column 726. Selecting the expansion button shows other documents that are similar to search result. Each search result also has a rank 728, a query-responsiveness score 730, an document age 732, a date 734, clinical-context information 736, a document title 738, the clinician that authored or authenticated the search result 740, and text summarizing the search result 742. The first search result is displayed first because it has the highest query-responsiveness score, which in this case is 1.00 746. The highest ranked search result is designated as number 1 744 in the list. The document age is 3 yrs 748, the date of the document is Oct. 4, 2007 750, the clinical-usage context of the document 752 is "Cardio Assoc. of Olathe/MD Consult." The title of the document 754 is "Cardiac Cath Evaluation." The clinician is Tom Clark 756. The text excerpts 722 for the first search results includes use of the clinical concept heart disease 633. The search results are based on matching criteria of related concepts 656. Clinical concepts related to heart disease are outlined in the text excerpts. The outlined text includes "heart disease" 758, "heart disease" 759, "heart disease" 760, "coronary artery disease" 761, and "occluded right coronary artery" 762.

The second search result is designated as search result number two 768, and has a query-responsiveness score 769 of 0.540. The document age is 3 yrs 770, and the date is Oct. 4, 2007. The clinical-usage context is "Beacon Health/MD Consult" 772 and the title of the document is "Card consult: exertional angina" 773. The clinician responsible for the second search result is Jordan Jones 774. The text excerpts 724 show outlined text that matches the search query 733. The outlined text includes "heart disease" 775, "coronary artery disease" 776, "angina" 777, "angina" 778, "coronary artery disease" 779, "heart disease" 780, and "sinus BR" 781.

The result interface 700 also includes a filter interface 785. The filter interface 785 allows the clinician to filter by year 786, encounter locations 787, or document class 788. The number of search results that match a particular filter criteria are displayed in parentheses adjacent to the suggested filter criteria. For example, 17 search results are available for the year 2007. The result interface 700 also includes query reset button 710 that allows the user to submit a new query. A sort-documents-by-date button 712 is also included in the search result interface 700.

Figure 5:
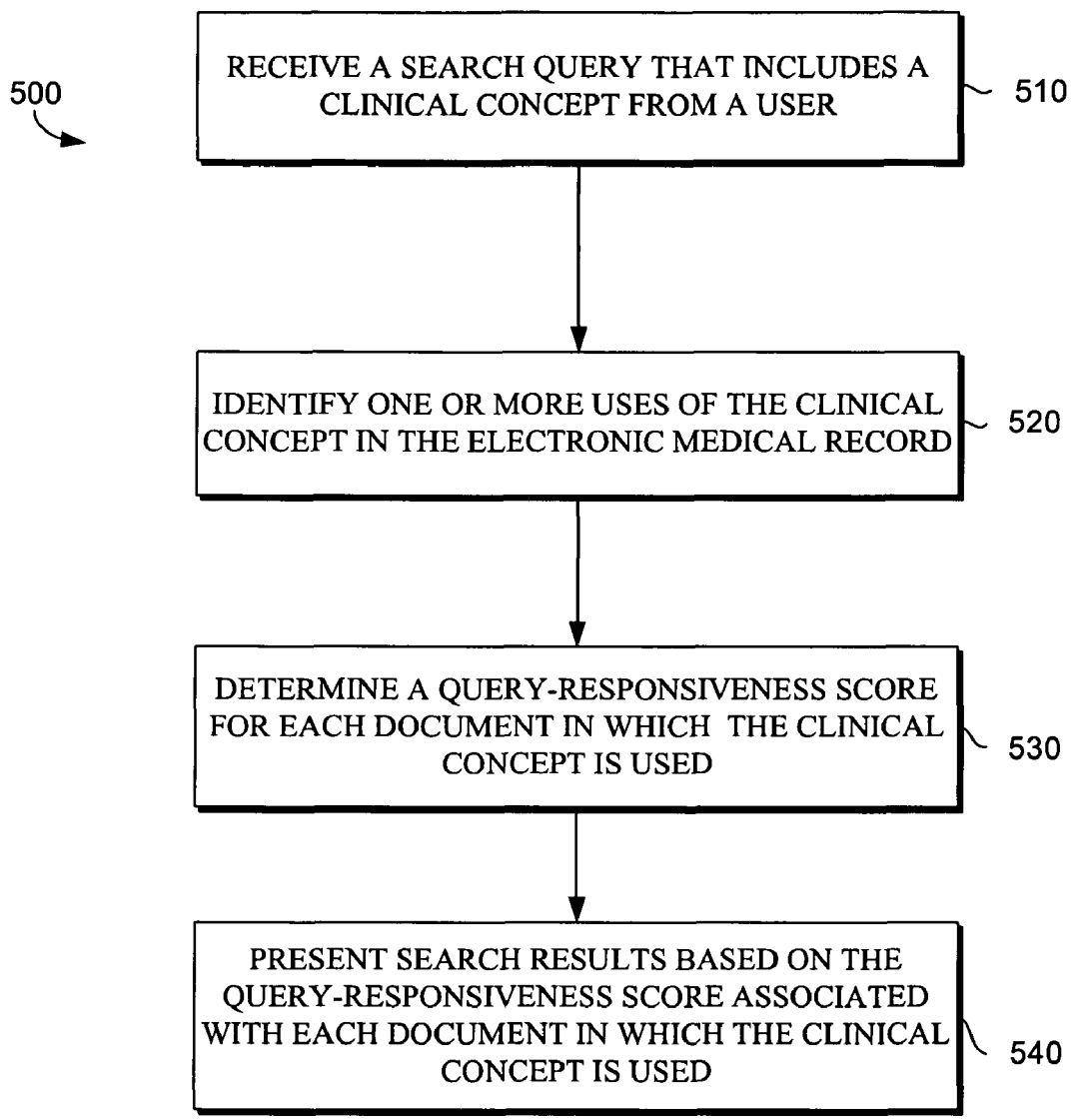
FIG. 5 is a flow diagram showing a method of searching an electronic medical record for a selected clinical concept, in accordance with an embodiment of the present invention.

Turning now to FIG. 5, a method 500 of searching an electronic medical record for a selected clinical concept is provided, in accordance with an embodiment of the present invention. At step 510, a search query that includes a clinical concept is received from a user. As described previously, the clinical concept describes any aspect of a person's health condition, or any object, action, attribute or idea that is related to a health condition. Examples include: diseases; symptoms; clinical observations and findings; diagnostic tests; diagnostic or therapeutic procedures; organisms, substances, devices or products related to health conditions; anatomic structures including genomic; phenotypic expression; behavior, family and social context related to health conditions; risk factors and outcomes; facilities and care providers. For example, heart disease and a heart attack are examples of clinical concepts. The search query may be received through an interface, such as search interface 600 described above with reference to FIG. 6. The clinical concept may be entered directly into the search interface word-for-word. In another embodiment, the clinician selects the clinical concept from a list of clinical concepts. In another embodiment, clinical concepts are derived from natural language text submitted into the search interface. The derivation of clinical concepts from natural language text may utilize a medical synonym dictionary. Any and all such variations, and any combination thereof, are contemplated to be within the scope of embodiments of the present invention.

At step 520, one or more uses of the clinical concept from the search query are identified in the electronic medical record. The electronic medical record is an electronic description of a medical history for a patient and is stored on one or more computer-readable media. In one embodiment, the clinical concepts within a medical record had previously been extracted and indexed. In this case, the index is searched for clinical concepts that match the clinical concept within the search query. As described previously the clinical concept from the search query could be an expanded-clinical concept.

At step 530, a query-responsiveness score is determined for each document within the electronic medical record that uses the clinical concept contained within the user's query. The query-responsiveness score describes how important a particular document or component is likely to be to the clinician. As described previously, the query-responsiveness score may be determined based on the combination of clinical-importance scores for each of the one more uses of the clinical concept and a set of boost factors calculated based on the expansions of the search query submitted by the clinician. The factors, such as clinical-usage context, specificity factor, frequency, truth status, and others that may be used to calculate the clinical-importance score have been described previously. Similarly, the factors utilized to calculate the boost factors have also been described previously. For example, the closeness-boost factor may be increased when the clinician that submitted the search query is in the same category of role as the clinician associated with the use of the clinical concept.

At step 540, search results are displayed based on the query-responsiveness score associated with each of the one or more uses of the clinical concept. The search result with the highest query-responsiveness score may be displayed first. Search results associated with lower query-responsiveness scores may be displayed subsequently.

As can be seen, embodiments of the present invention allow a user to submit a search query through an interface and return search results from an electronic medical record that are responsive to the search query. The search results by default will be ordered according to a query-responsiveness score so that the clinician will find the most important document at the top of the list.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more non-transitory computer-storage media having computer executable instructions embodied thereon that when executed by a computer perform a method of finding information in an electronic medical record, the method comprising:
receiving a search query from a user to search the electronic medical record, wherein the electronic medical record is associated with a patient, and wherein the electronic medical record includes a plurality of electronic documents that describe a medical history for the patient and is stored on the computer-storage media;

identifying one or more components of the electronic medical record that contain text that matches the search query, wherein each of the one or more components is a section of text within the electronic medical record that includes one or more words;

determining a query-responsiveness score for each of the one or more components that match the search query, wherein the query-responsiveness score indicates how responsive an individual component is to the search query, wherein determining the query-responsiveness score of each of the one or more components further comprises:

determining a patient-subject status for each particular-clinical concept recited in the one or more components, wherein the patient-subject status indicates whether the patient is an object of a particular-clinical concept recited in a particular component of the one or more components;

determining a truth status for said each particular-clinical concept recited in the one or more components, wherein the truth status indicates whether said each particular-clinical concept was expressed positively, negatively, ambiguously, or unknown;

determining a clinical-usage context for each particular-clinical concept recited in the one or more components, wherein the clinical-usage context describes how the clinical concept was used in the component;

determining a document-importance factor for each particular-clinical concept recited in the one or more components, wherein the document-importance factor measures the relevance of the particular-clinical concept to the main subject of a particular document by analyzing other clinical concepts that are used in the particular document with the particular-clinical concept;

determining a specificity factor for each particular-clinical concept recited in the one or more components based on a degree of narrowness for a scope of said each particular-clinical concept; and presenting search results that communicate information describing each of the one or more components, wherein the search results are displayed ordered according to the query-responsiveness score assigned to each of the one or more components.

2. The media of claim 1, wherein the method further includes receiving a selection of a search mode, wherein the search mode is set to match related concepts, and wherein the one or more components of the electronic medical record matches the search query when a clinical concept conveyed by the search query matches at least one related clinical concept recited in the one or more components of the electronic medical record, and wherein the clinical concept describes any aspect of a person's health condition.

3. The media of claim 2, wherein determining the query-responsiveness score of each of the one or more components further includes:

wherein the query-responsiveness score for the individual component is increased when the patient-subject status for one or more of the clinical concepts identified within the component is affirmative, when the truth status for one or more of the clinical concepts identified within the component equals positive, when the clinical-usage context for one or more of the clinical concepts identified within the component directly relates to the patient, when the document-importance factor is high, and when the specificity factor for one or more of the clinical concepts identified within the component is high.

4. The media of claim 1, wherein the method further includes displaying one or more filter options that allows the user to filter the search results, wherein the one or more filter options are based on one or more of a clinical-concept in an individual search result, an aggregation of related clinical concepts, a clinical facility associated with the individual search result, and a document class associated with the individual search result.

5. The media of claim 1, wherein the method further includes receiving a selection of a search mode, wherein the search mode is a medical synonym match, wherein the one or more components of the electronic medical record matches the search query when at least a medical synonym of the one or more words in the search query is found within the one or more components of the electronic medical record, and wherein the medical synonyms match search mode includes matching two or more words or phrases that have a similar medical meaning.

6. The media of claim 1, wherein the method further includes:

expanding one or more primary clinical concepts recited in the search query to additional related clinical concepts, thereby generating a plurality of expanded clinical concepts to match with a particular one of the one or more components of the electronic medical record;

assigning a boost factor to each combination of an expanded clinical concept and the particular matching component of the electronic medical record, wherein the boost factor is higher when the expanded clinical concept is close to the one or more primary clinical concepts on a clinical-concept ontology and lower when the expanded clinical concept is remote from the one or more primary clinical concepts; and wherein the boost factor is used to calculate the query-responsiveness score for said each combination of the expanded clinical concept and the particular-clinical concepts contained within the matching component.

7. The media of claim 1, wherein the method further includes increasing the query-responsiveness score when a role of the user who submitted the search query is in the same category as the role of a person that created a matching component.

8. One or more non-transitory computer-storage media having computer executable instructions embodied thereon that when executed by a computer perform for performing a method of searching an electronic medical record for clinical concepts, the method comprising:

receiving a search query that includes a clinical concept from a user to search the electronic medical record, wherein the clinical concept is an aspect related to a person's health, wherein the electronic medical record is associated with a patient, and wherein the electronic medical record includes a plurality of electronic documents that describe a medical history for the patient and is stored on the computer-storage media;

identifying one or more uses of the clinical concept in the electronic medical record, wherein a use of a clinical concept is a single occurrence of the clinical concept within the electronic medical record, wherein the documents in the electronic medical record describe the patient's medical history, and wherein the electronic medical record is stored on the computer-storage media;

determining a clinical-importance score for each of the one or more uses of the clinical concept, wherein the clinical-importance score quantifies how important each use of the clinical concept is likely to be to the user querying the electronic medical record, and wherein the clinical-importance score is calculated based on the use of the clinical concept within the electronic medical record and without reference to any specific search query;

determining at least one boost factor for each of the one or more uses of the clinical concept, wherein the at least one boost factor is based on the search query and the user, wherein the at least one boost factor includes a role-boost factor, wherein each role-boost factor is based on a role of the user that submitted the search query and a role of a person that generated the particular use of the clinical concept in the electronic medical record, and wherein the particular role-boost factor is increased when the role of the user is in the same category as the role of the person associated with the use of the clinical concept within the electronic medical record;

calculating a query-responsiveness score for each document within the electronic medical record in which the clinical concept is used by combining the one or more clinical-importance scores with the one or more boost factors; and presenting search results based on the query-responsiveness score associated with each said document within the electronic medical record in which the one or more uses of a clinical concept was identified, wherein the search results are displayed ordered according to the query-responsiveness score.

9. The media of claim 8, wherein the method further includes:
determining a clinical-usage context for each use of the clinical concept in the electronic medical record, wherein the clinical-usage context describes how the clinical concept was used in each document of the electronic medical record;
determining a truth status for each use of the clinical concept in the electronic medical record, wherein the truth status indicates whether the clinical concept was expressed in as one of positively, negatively, ambiguously, and unknown; and
wherein the clinical-importance score for said each of the one or more uses of the clinical concept is based on the clinical-usage context and the truth status for said each of the one or more uses of the clinical concept.

10. The media of claim 9, wherein the method further includes:
determining a patient-subject status for each use of the clinical concept in the documents of the electronic medical record, wherein the patient-subject status indicates whether or not the patient is an object of the particular use of the clinical concept; and
wherein the clinical-importance score for said each of the one or more uses of the clinical concept in said each of the one or more documents in the electronic medical record is based on the clinical-usage context, the truth status, and the patient-subject status for said each of the one or more uses of the clinical concept.

11. The media of claim 10, wherein the method further includes:
determining a specificity factor for the particular use of the clinical concept based on a degree of narrowness for a scope of the particular use of the clinical concept;
determining a document-importance factor for the particular use of the clinical concept, wherein the document-importance factor measures the relevance of the particular use of the clinical concept to the main subject of a particular document by analyzing other clinical concepts that are used in the particular document with the particular use of the clinical concept; and
wherein the clinical-importance score for said each of the one or more uses of the clinical concept is based on the clinical-usage context, the truth status, the patient-subject status, the document-importance factor, and the specificity factor for the particular use.

12. The media of claim 8, wherein the at least one boost factor includes a clinical-facility-boost factor, wherein the clinical-facility-boost factor is based on a clinical facility associated with the user that submitted the search query and the clinical facility associated with a use of the clinical concept in the electronic medical record, and wherein a clinical-facility-boost factor is increased for the use of the clinical concept in the electronic medical record when the use of the clinical concept in the electronic medical record is in a portion of the electronic medical record that is associated with the clinical facility from which the user submitted the search query.

13. The media of claim 8, wherein the method further includes:
expanding the clinical concept recited in the search query into additional related clinical concepts, thereby generating a plurality of expanded clinical concepts to match to each of the uses of the plurality of expanded clinical concepts within documents in the electronic medical record;
assigning a closeness-boost factor to each combination of an expanded-clinical concept and a matching use of the expanded-clinical concept within a document in the electronic medical record, wherein the closeness-boost factor is higher when the expanded-clinical concept is close to the clinical concept on a clinical-concept ontology and lower when the expanded clinical concept is remote from the clinical concept; and
wherein the at least one boost factor includes the closeness-boost factor.

* * * * *